(12) United States Patent
Bordeaux

(10) Patent No.: US 9,273,715 B2
(45) Date of Patent: Mar. 1, 2016

(54) OUTRIGGER WITH LOCKING MECHANISM

(71) Applicant: SYNTHES USA, LLC, West Chester, PA (US)

(72) Inventor: Jean-Noel Bordeaux, West Chester, PA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 24 days.

(21) Appl. No.: 13/775,706

(22) Filed: Feb. 25, 2013

(65) Prior Publication Data

US 2013/0165931 A1    Jun. 27, 2013

Related U.S. Application Data

(63) Continuation of application No. 12/782,938, filed on May 19, 2010, now Pat. No. 8,403,928, and a continuation of application No. 11/114,554, filed on Apr. 25, 2005, now Pat. No. 7,722,609.

(51) Int. Cl.
| | |
|---|---|
| *A61B 17/60* | (2006.01) |
| *F16B 39/24* | (2006.01) |
| *F16B 39/282* | (2006.01) |
| *A61B 17/64* | (2006.01) |
| *A61B 19/00* | (2006.01) |

(52) U.S. Cl.
CPC ............... *F16B 39/24* (2013.01); *A61B 17/60* (2013.01); *A61B 17/6466* (2013.01); *F16B 39/282* (2013.01); *A61B 17/64* (2013.01); *A61B 2019/304* (2013.01)

(58) Field of Classification Search
CPC .... A61B 17/60; A61B 17/64; A61B 17/6466; F16B 39/24

USPC ............. 606/53–55, 57, 59, 271, 277
See application file for complete search history.

(56) References Cited

U.S. PATENT DOCUMENTS

| | | | |
|---|---|---|---|
| 1,427,807 A | 9/1922 | Halbleib | |
| 2,238,870 A | 4/1941 | Haynes | |
| 2,250,417 A | 7/1941 | Ettinger | |
| 2,251,209 A | 7/1941 | Stader | |
| 2,346,346 A | 4/1944 | Anderson | |
| 2,391,537 A * | 12/1945 | Anderson | ........... 606/59 |

(Continued)

FOREIGN PATENT DOCUMENTS

EP    0265569    5/1988

*Primary Examiner* — Christopher Beccia
(74) *Attorney, Agent, or Firm* — Fay Kaplun & Marcin, LLP

(57) ABSTRACT

A method is for connecting an outrigger to a clamp in an external fixation system. A moveable member and a slide lock are coupled to an elongated member of the outrigger. The elongated member has a length, a distal end, a proximal end and a threaded portion on the distal end. The threaded portion has a keyed portion. The moveable member is moveable along the elongated member. The slide lock has a keyed portion and an engagement surface. The distal end of the elongated member is coupled to an opening of the clamp such that the engagement surface of the slide lock engages a portion of the clamp. The keyed portion of the threaded portion and the keyed portion of the slide lock are operably associated with each other to permit longitudinal movement of the slide lock along the length of the elongated member while preventing rotation. The engagement surface of the slide lock has a non-smooth texture and faces in a direction that is away from the moveable member.

17 Claims, 5 Drawing Sheets

(56) References Cited

U.S. PATENT DOCUMENTS

| | | |
|---|---|---|
| 4,349,017 A | 9/1982 | Sayegh |
| 4,365,624 A | 12/1982 | Jaquet |
| 4,456,004 A | 6/1984 | Kenny |
| 4,483,334 A | 11/1984 | Murray |
| 4,535,763 A | 8/1985 | Jaquet |
| 4,541,422 A | 9/1985 | De Zbikowski |
| 4,584,995 A | 4/1986 | Koeneman |
| 4,600,000 A | 7/1986 | Edwards |
| 4,612,921 A | 9/1986 | De Zbikowski |
| 4,848,368 A | 7/1989 | Kronner |
| 4,919,119 A | 4/1990 | Jonsson et al. |
| 4,922,896 A | 5/1990 | Agee et al. |
| 4,941,481 A | 7/1990 | Wagenknecht |
| 5,047,029 A | 9/1991 | Aebi et al. |
| 5,098,432 A | 3/1992 | Wagenknecht |
| 5,122,140 A | 6/1992 | Asche et al. |
| 5,275,599 A | 1/1994 | Zbikowski et al. |
| 5,312,403 A | 5/1994 | Frigg |
| 5,330,474 A | 7/1994 | Lin |
| 5,393,161 A | 2/1995 | Mata et al. |
| 5,397,322 A | 3/1995 | Campopiano |
| 5,429,637 A | 7/1995 | Hardy |
| 5,624,440 A * | 4/1997 | Huebner .................. 606/59 |
| 5,630,815 A | 5/1997 | Pohl et al. |
| 5,752,954 A | 5/1998 | Mata et al. |
| 5,803,924 A | 9/1998 | Oni et al. |
| 5,921,985 A | 7/1999 | Ross, Jr. et al. |
| 6,010,501 A | 1/2000 | Raskin et al. |
| 6,022,348 A | 2/2000 | Spitzer |
| 6,080,153 A | 6/2000 | Mata et al. |
| 6,217,577 B1 | 4/2001 | Hofmann |
| 6,277,119 B1 | 8/2001 | Walulik et al. |
| 6,409,729 B1 | 6/2002 | Martinelli et al. |
| 6,428,540 B1 | 8/2002 | Claes et al. |
| 6,482,206 B2 | 11/2002 | Schoenefeld |
| 6,565,564 B2 | 5/2003 | Hoffman et al. |
| 6,613,049 B2 | 9/2003 | Winquist et al. |
| 6,616,664 B2 | 9/2003 | Walulik et al. |
| 6,702,814 B2 | 3/2004 | Walulik et al. |
| 6,746,448 B2 | 6/2004 | Weiner et al. |
| 7,261,713 B2 * | 8/2007 | Langmaid et al. .............. 606/59 |
| 2003/0191467 A1 | 10/2003 | Hoffmann-Clair et al. |
| 2003/0191468 A1 | 10/2003 | Hoffman et al. |
| 2004/0044344 A1 | 3/2004 | Winquist et al. |
| 2004/0059331 A1 | 3/2004 | Mullaney |
| 2004/0097922 A1 | 5/2004 | Mullaney |
| 2005/0059549 A1 | 3/2005 | Vo |

* cited by examiner

OUTRIGGER WITH LOCKING MECHANISM

PRIORITY CLAIM

The present application is a Continuation application of U.S. patent application Ser. No. 12/782,938 filed on May 19, 2010 which is a Continuation application of U.S. patent application Ser. No. 11/114,554 filed on Apr. 25, 2005 (now U.S. Pat. No. 7,722,609). The disclosure of the above application and patent is incorporated herein by reference.

FIELD OF THE INVENTION

The present invention relates to an outrigger for use in an external fixation system and, in particular, a locking mechanism which prevents loosening of the outrigger after surgery.

BACKGROUND OF THE INVENTION

Outriggers typically form part of an external fixation system and are usually attached to a clamp which holds one or more wires, pins, screws, rods, bars and/or rings. Threads on one end of the outrigger have been used to attached the outrigger to a clamp. Such a construction, however, may allow the outrigger to loosen and/or separate from the clamp after a surgical procedure. Therefore, it is desirable to have an outrigger incorporating a locking mechanism which prevents the outrigger from loosening and/or separating from a clamp after surgery.

SUMMARY OF THE INVENTION

The present invention relates to an outrigger which may include an elongated member having a distal end, a proximal end and a connecting portion proximate the distal end; a moveable member operably associated with the distal end; and a slide lock. In one embodiment, the connecting portion may be a threaded portion.

The threaded portion may have a keyed portion (e.g., at least one flat side) and may be screwed into a threaded opening in a clamp. The slide lock may have an opening therethrough which may be keyed or configured such that it can translate along the threaded portion but not rotate about the threaded portion. In one embodiment, the slide lock may have an opening therethrough with at least one flat portion which may cooperate with at least one flat side of the threaded portion.

The moveable member may be positioned proximal the slide lock such that the slide lock may be positioned between the moveable member and a clamp. The moveable member may engage the threaded portion of the elongated member such that the moveable member may move distally and proximally along the threaded portion. In one embodiment, the movement member may be a nut having an opening with internal threads, which may engage the threaded portion. Rotation of the nut may move the nut towards and/or away from the slide lock. Movement of the moveable portion towards the slide lock may push the slide lock distally such that the slide lock may translate along the threaded portion towards a clamp.

The slide lock may have an engagement portion such as, for example, a serrated, knurled or rough surface. As the moveable member moves the slide lock distally along the threaded portion, the engagement portion of the slide lock may engage a surface of a clamp, which may be a serrated, knurled or rough surface. Contact between the engagement portion of the slide lock and the surface of the clamp may prevent rotational movement of the slide lock relative to the clamp. Because of the configuration, such as, for example, the keyed configuration of the opening in the slide lock, rotational movement of the outrigger with respect to the slide lock and, consequently, the clamp may also be prevented. In one exemplary embodiment, at least one flat portion of the slide lock may engage the flat, unthreaded side of the threaded portion to prevent rotation of the outrigger with respect to the slide lock and, consequently, rotation of the outrigger with respect to the clamp.

In one embodiment, the threaded portion of the elongated member of the outrigger may have a groove for receiving a washer, which may limit the extent the threaded portion may be screwed into a clamp. The washer may also keep the moveable portion and slide lock from sliding off the elongated member so that the elongated member, moveable portion and slide lock may be attached to a clamp as an assembly that cannot be readily disassembled, or may only be disassembled by breaking one or more pieces of the assembly.

In use, the elongated member, moveable member and slide lock may be connected together. The moveable member may be positioned proximate the slide lock such that the slide lock may be located between the moveable member and a clamp. The threaded portion may be screwed into a threaded opening in a clamp. In an embodiment incorporating a washer around the threaded portion, the threaded portion may be screwed into the clamp until the washer contacts the clamp. Thereafter, the moveable member may be moved in a distal direction towards the slide lock and the clamp. The moveable member, in turn, may move the slide lock towards the clamp until the engagement portion of the slide lock engages a portion of the clamp. The moveable member may be tightened to fix the position of the slide lock and, consequently, the elongated member relative to the clamp.

In one embodiment, a method for inserting an outrigger to a clamp of an external fixation system may comprise providing an outrigger which may have an elongated member having a length, a distal end, a proximal end and a connecting portion on the distal end, wherein the connecting portion may have a keyed portion; a moveable member operably associated with the elongated member which may be moveable along the elongated member; and a slide lock which may be disposed about the elongated member, the slide lock may have a keyed portion and an engagement surface, wherein the keyed portion of the connecting portion and the keyed portion of the slide lock may be operably associated with each other to permit longitudinal movement of the slide lock along the length of the elongated member while preventing rotation, and wherein the engagement surface of the slide lock may be configured to engage a portion of a clamp. The method may further comprise providing a clamp which may have an opening and an engagement portion positioned proximate the opening, moving the connecting portion of the elongated member into the opening of the clamp, engaging the connecting portion to the clamp, moving the moveable member on the connecting portion to move the slide lock towards the clamp, and engaging the engagement surface of the slide lock with the engagement portion of the clamp. Moreover, in an embodiment where the connecting portion may further comprise a groove for receiving a washer, the method may also comprise moving the connecting portion into the opening until the washer contacts the engagement portion of the clamp.

In an embodiment where the connecting portion may be a threaded portion, the method may further comprise providing a clamp which may have a threaded opening and an engagement portion positioned proximate the opening, screwing the threaded portion of the elongated member into the threaded opening of the clamp, moving the moveable member on the threaded portion to move the slide lock towards the clamp, and engaging the engagement surface of the slide lock with the engagement portion of the clamp. Furthermore, in an embodiment where the threaded portion may further comprise a groove for receiving a washer, the method may also comprise screwing the threaded portion into the threaded opening until the washer contacts the engagement portion of the clamp.

BRIEF DESCRIPTION OF THE DRAWINGS

The present invention can be better understood by reference to the following drawings, wherein like references numerals represent like elements. The drawings are merely exemplary to illustrate certain features that may be used singularly or in combination with other features and the present invention should not be limited to the embodiments shown.

DETAILED DESCRIPTION

Figure 1:
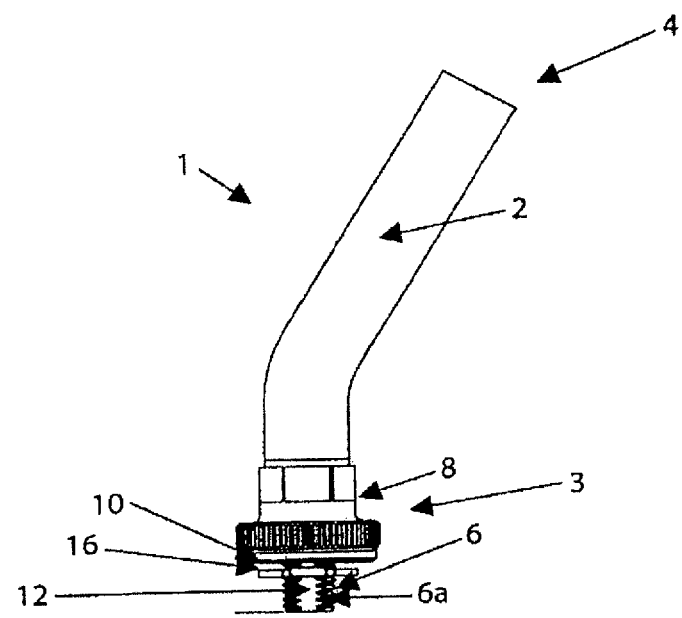
FIG. 1 is a side view of an exemplary embodiment of the outrigger of the present invention.

As shown in FIG. 1, the outrigger 1 may include an elongated member 2 having a distal end 3, a proximal end 4 and a connecting portion 6 proximate the distal end 3; a moveable member 8 operably associated with the distal end 3; and a slide lock 10. It should, however, be understood that those of ordinary skill in the art will recognize many modifications and substitutions which may be made to various elements of the present invention.

The elongated member 2, moveable member 8 and slide lock 10 may be made of any material, preferably, a biocompatible material such as, for example, metal (e.g., stainless steel, titanium, aluminum), plastic, rubber, ceramic, an alloy of two or more materials, or a composite material (i.e., made up of two or more materials). The elongated member 2, moveable member 8 and slide lock 10 may be made of the same or different materials.

Figure 2:
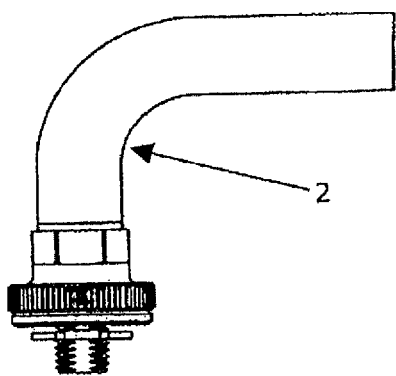
FIG. 2 is a side view of an alternative exemplary embodiment of the outrigger of FIG. 1.

The elongated member 2 may be straight or bent at an angle. As illustrated in FIGS. 1 and 2, the elongated member 2 may be bent at an angle θ of, for example, between about 90 degrees and about 180 degrees, preferably, between about 115 degrees and about 170 degrees and, most preferably, between about 140 degrees and about 160 degrees. The elongated member 2 may be solid or hollow.

Figure 3A:
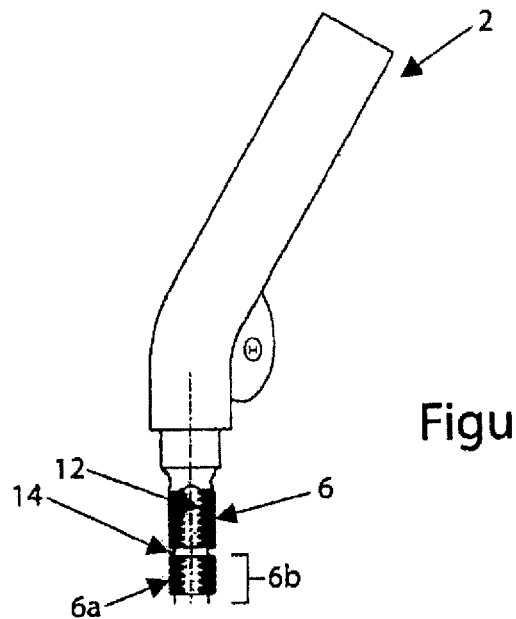
FIGS. 3A-C are side views of an exemplary embodiments of a component of the present invention.

In one embodiment, the connecting portion 6 may be a threaded portion. The threaded portion 6 may have a keyed portion 12 or may otherwise have a non-circular cross-section for reasons that will be explained below. As shown in FIGS. 1 and 3A, the keyed portion 12 of the threaded portion 6 of the elongated member 2 may take the form of at least one flat side 12. In a preferred embodiment, the threaded portion 6 may have two diametrically opposed flat sides 12. Moreover, the threaded portion 6 may also have a circumferential, unthreaded groove 14 for receiving a washer 16. The washer 16 may limit the extent to which a surgeon may screw the outrigger 1 into a clamp (e.g., clamp 100 of FIGS. 5 and 6). In addition, the washer 16 may keep the moveable member 8 and the slide lock 10 from sliding off the elongated member 2 so that the elongated member 2, moveable member 8 and the slide lock 10 may be attached to a clamp as an assembled, single unit. The washer 16 may be made of any of metal (e.g., stainless steel, titanium, aluminum), plastic, rubber, ceramic, an alloy of two or more materials, or a composite material (i.e., made up of two or more materials). In a preferred embodiment, the washer 16 may be made of metal.

Figure 3B:
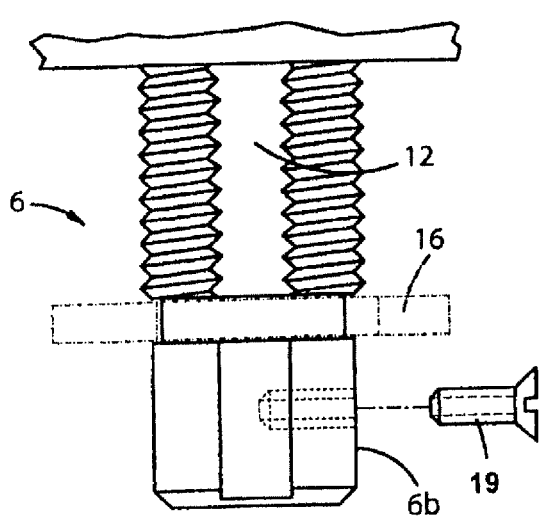
Figure 3C:
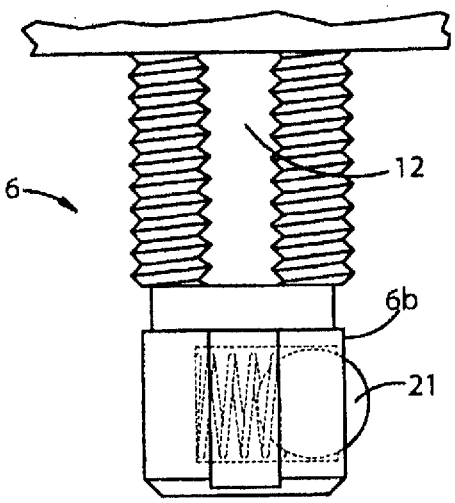

It will be appreciated by those skilled in the art that the connecting portion 6 may be configured in any manner so long as the connecting portion 6 may prevent the elongated member 2 from being removed from a clamp (e.g., clamp 100, FIGS. 5 and 6) and may allow for attachment of the moveable member 8 to the elongated member 2. In one embodiment, the lower portion 6b of the connecting portion 6 may be unthreaded and may have a portion (e.g., a flat surface, an indentation, an opening), which may be engaged by a set screw 19 (FIG. 3B) positioned through a clamp. The set screw 19 may hold the elongated member 2 to the clamp. In another embodiment, the connecting portion 6 may comprise a retractable member (e.g., ball detent) 21 (FIG. 3C) which may be in a retracted position as the connecting portion 6 is inserted into an opening of a clamp and which may expand to fix the elongated member 2 to the clamp once the connecting portion 6 has been inserted a distance into the opening of the clamp.

Figure 4A:
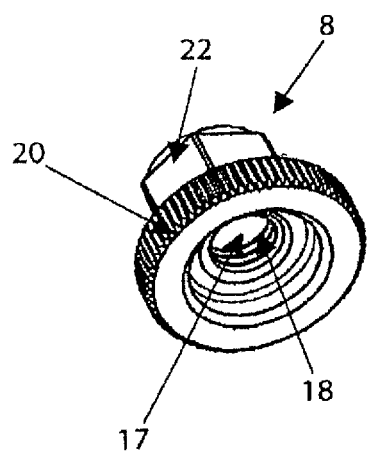
FIGS. 4A and 4B are perspective views of an exemplary embodiment of additional components of the present invention.

A moveable member 8 may be attached to the threaded portion 6. As shown in FIG. 4A the moveable member 8 may have an opening 17 with internal threads 18. The internal threads 18 may engage external threads 6a on the threaded portion 6 such that rotation of the moveable member 8 in a first direction may result in the moveable member 8 moving towards the distal end 3 and rotation of moveable member 8 in a second direction may result in the moveable member 8 moving towards the proximal end 4. The moveable member 8 may also have a gripping portion 20 and a tightening portion 22. The gripping portion 20 may be used by a surgeon to tighten the moveable member 8 to a clamp using the surgeon's fingers. The gripping portion 20 may have numerous grooves or other surface roughening or enhancements to improve a surgeon's grip on the moveable member 8. To further tighten the moveable member 8 to a clamp, the surgeon may use a tool to engage tightening portion 22. The tightening portion 22 may be any shape (e.g., square, hexagon, octagon). It will be appreciated by those skilled in the art that the moveable member 8 may be any component which may be moved up and down the threaded portion 6 and fixed in position on the threaded portion 6, and may comprise a nut.

Figure 4B:
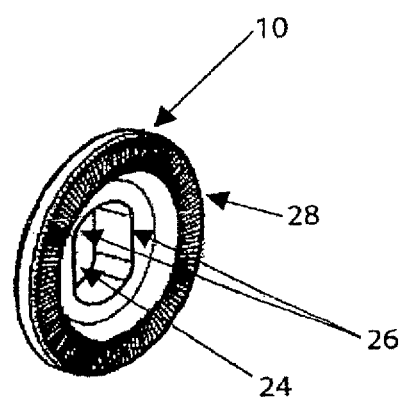

The slide lock 10 (FIG. 4B) may be positioned proximate the moveable member 8 and, in particular, may be positioned between the moveable member 8 and a clamp. The slide lock 10 may have an opening 24 which may receive the threaded portion 6. The opening 24 may be keyed or otherwise configured to cooperate with the keyed portion of the threaded portion 6 so that the slide lock 10 may translate along the threaded portion 6, but not rotate thereabout. In one embodiment, the opening 24 may have at least one flat portion 26 which may cooperate with the at least one flat side 12 of the threaded portion 6 such that the slide lock 10 may translate along the threaded portion 6, but not rotate thereabout. In a preferred embodiment, the slide lock 10 may have two diametrically opposed flat portions 26 to engage two diametrically opposed flat sides 12 of the threaded portion 6. It should be noted, however, that any configuration of the slide lock 10 and threaded portion 6 may be used so long as the slide lock 10 may be prevented from rotating with respect to the threaded portion 6.

Figure 5:
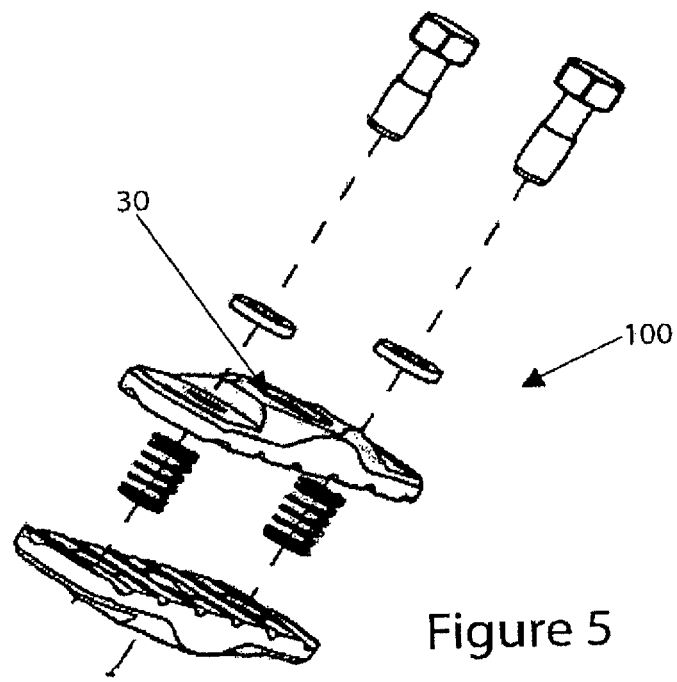
FIG. 5 is a perspective, exploded view of an exemplary embodiment of a clamp used in an external fixation system.
Figure 6:
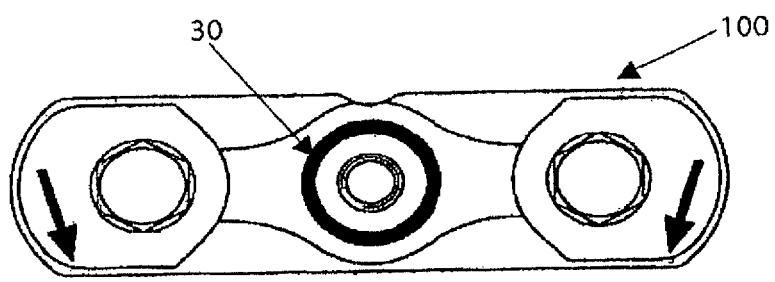
FIG. 6 is a top view of the clamp of FIG. 5.

The slide lock 10 may have an engagement portion 28 such as, for example, a serrated, knurled or rough surface. The engagement portion 28 of the slide lock 10 may be integral with the slide lock 10 or may be a separate piece. The engagement portion 28 may contact a portion of a clamp. In one embodiment, the engagement portion 28 may be serrated and may engage the serrations 30 on either side of a clamp 100 (FIGS. 5 and 6). It will be appreciated that the engagement portion 28 of the slide lock 10 may be configured to include a surface which may provide sufficient friction when engaged with a surface of a clamp so as to prevent the slide lock 10 from moving (e.g., rotating) with respect to the clamp. Although shown as a relatively flat disc, the slide lock 10 may take the form of other shapes.

In use, the elongated member 2, moveable member 8 and slide lock 10 may be operably connected to each other. The threaded portion 6 of the elongated member 2 may be twisted or screwed into a threaded opening in a clamp. In an embodiment that includes the optional washer 16, the elongated member 2 may be screwed into the clamp until the washer 16 engages the clamp. The moveable member 8 may be rotated such that the moveable member 8 moves towards the clamp and, thus, may move the slide lock 10 towards the clamp. The keyed configuration of the threaded portion 6 and the slide lock 10 may allow the slide lock 10 to translate without rotating. For example, the engagement of the at least one flat side 12 of the threaded portion 6 with the at least one flat portion 26 of the slide lock 10 may result in the slide lock 10 translating along the threaded portion 6, while preventing the slide lock 10 from rotating about the threaded portion 6. As the slide lock 10 moves closer to the clamp, the engagement portion 28 of the slide lock 10 may engage a surface of the clamp. In an embodiment where the engagement portion 28 may be serrated, these serrations may engage corresponding serrations on the clamp. When the slide lock 10 engages the clamp, the slide lock 10 may be fixed or locked relative to the clamp and rotation between the slide lock 10 and the clamp may be prevented. Moreover, the engagement between the at least one flat side 12 and the at least one flat portion 26 may prevent the elongated member 2 from rotating with respect to slide lock 10 and, consequently, also with respect to the clamp. Such a construction may help prevent the outrigger 1 from loosening or separating from a clamp after surgery.

Figure 7:
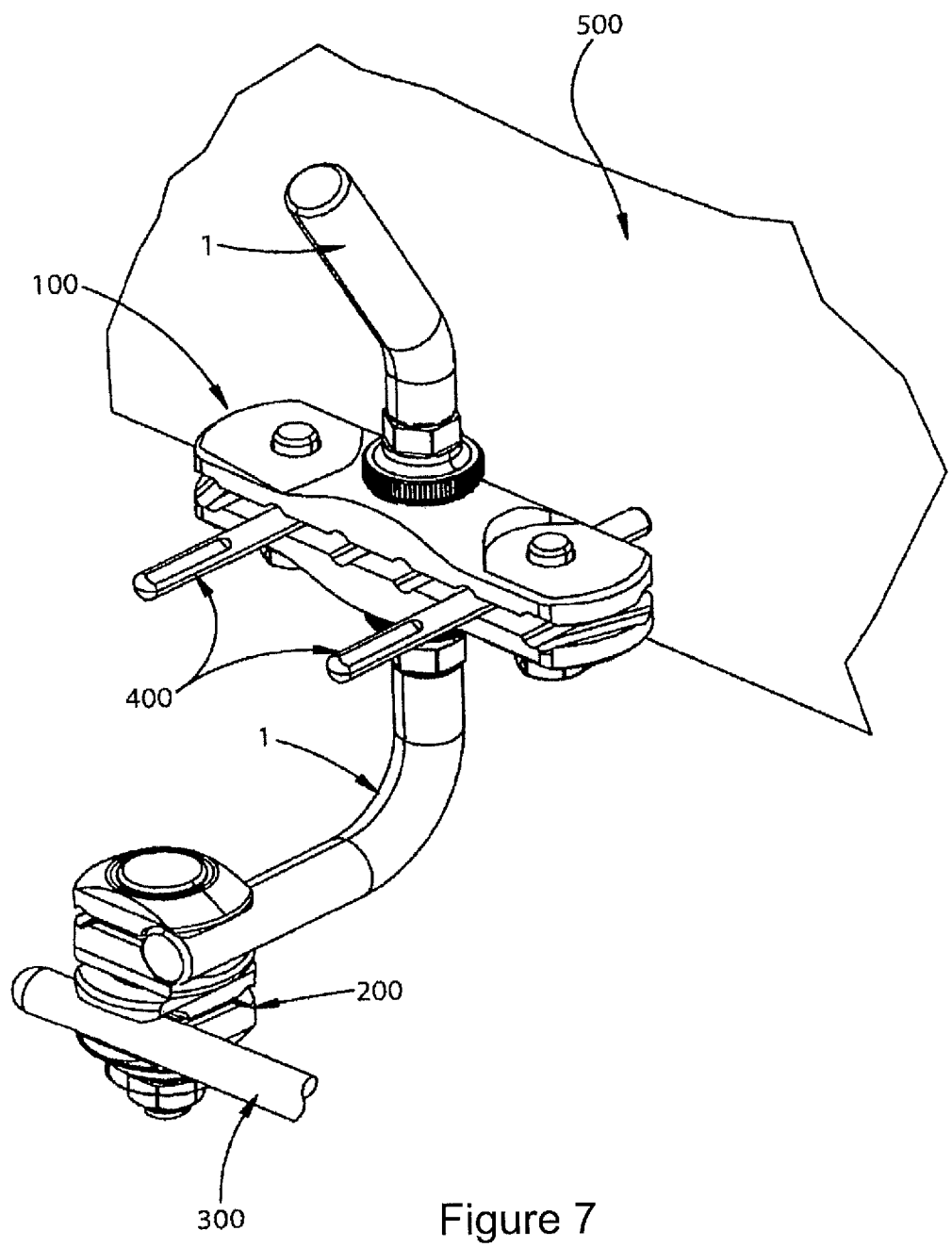
FIG. 7 is a perspective view of an exemplary embodiment of an external fixation system incorporating the devices of FIGS. 1, 2 and 5.

As shown in FIG. 7, the outrigger 1 may be used to connect various components including, for example, a clamp 200 and rod 300, to a pin clamp 100, which may engage pins or wires 400 inserted in a bone 500. The outrigger 1 may be used as a component of an external fixation device.

While the foregoing description and drawings represent the preferred embodiments of the present invention, it will be understood that various additions, modifications and substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being indicated by the appended claims, and not limited to the foregoing description.

What is claimed is:

1. A method for connecting an outrigger to a clamp in an external fixation system, comprising:
    coupling a moveable member and a slide lock to an elongated member of the outrigger, the elongated member having a length, a distal end, a proximal end and a threaded portion on the distal end, the threaded portion having a keyed portion, the moveable member being moveable along the elongated member, the slide lock having a keyed portion and an engagement surface; and
    coupling the distal end of the elongated member to an opening of the clamp such that the engagement surface of the slide lock engages a portion of the clamp,
    wherein the keyed portion of the threaded portion and the keyed portion of the slide lock are operably associated with each other to permit longitudinal movement of the slide lock along the length of the elongated member while preventing rotation, and
    wherein the engagement surface of the slide lock has a non-smooth texture and faces in a direction that is away from the moveable member.

2. The method of claim 1, wherein the engagement surface is serrated.

3. The method of claim 1, wherein the engagement surface is knurled.

4. The method of claim 1, wherein the keyed portion of the threaded portion is at least one flat side.

5. The method of claim 4, wherein the keyed portion of the slide lock is at least one flat portion.

6. The method of claim 1, wherein the clamp engages at least one fixation element.

7. The method of claim 6, wherein the at least one fixation element includes at least one of a screw, a pin, a wire, a rod, a bar, and a ring.

8. A method for connecting an outrigger to a clamp in an external fixation system, comprising:
    coupling a moveable member and a slide lock to an elongated member of the outrigger, the elongated member having a length, a distal end, a proximal end and a threaded portion on the distal end, the threaded portion having a keyed portion and a groove, the moveable member being moveable along the elongated member, and the slide lock having a keyed portion and an engagement surface; and
    coupling the distal end of the elongated member to an opening of the clamp such that the engagement surface of the slide lock engages a portion of the clamp,
    wherein the keyed portion of the threaded portion and the keyed portion of the slide lock are operably associated with each other to permit longitudinal movement of the slide lock along the length of the elongated member while preventing rotation, and
    wherein a washer is received in the groove.

9. A method for connecting an outrigger to a clamp in an external fixation system, comprising:
    coupling a moveable member and a slide lock to an elongated member of the outrigger, the elongated member having a length, a distal end, a proximal end and a connecting portion on the distal end, the connecting portion having a keyed portion, the moveable member being moveable along the elongated member, the slide lock having a keyed portion and an engagement surface; and coupling the distal end of the elongated member to an opening of the clamp such that the engagement surface of the slide lock engages a portion of the clamp, wherein the keyed portion of the connecting portion and the keyed portion of the slide lock are operably associated with each other to permit longitudinal movement of the slide lock along the length of the elongated member while preventing rotation, and wherein the engagement surface of the slide lock has a non-smooth texture and faces in a direction that is away from the moveable member.

10. The method of claim 9, wherein the engagement surface is serrated.

11. The method of claim 10, wherein the engagement surface is knurled.

12. The method of claim 10, wherein the keyed portion of the connecting portion is at least one flat side.

13. The method of claim 12, wherein the keyed portion of the slide lock is at least one flat portion.

14. The method of claim 10, wherein the connecting portion is sized and configured to engage a set screw.

15. The method of claim 10, wherein the connecting portion comprises a threaded portion.

16. A method for connecting an outrigger to a clamp in an external fixation system, comprising:

coupling a moveable member and a slide lock to an elongated member of the outrigger, the elongated member having a length, a distal end, a proximal end and a connecting portion on the distal end, the connecting portion having a keyed portion and a groove, the moveable member being moveable along the elongated member, and the slide lock having a keyed portion and an engagement surface; and coupling the distal end of the elongated member to an opening of the clamp such that the engagement surface of the slide lock engages a portion of the clamp, wherein the keyed portion of the connecting portion and the keyed portion of the slide lock are operably associated with each other to permit longitudinal movement of the slide lock along the length of the elongated member while preventing rotation, wherein the engagement surface is knurled, and wherein a washer is received in the groove.

17. The method of claim 16, wherein the connecting portion comprises a retractable member.

* * * * *